United States Patent
Beaupré et al.

(10) Patent No.: US 10,874,394 B2
(45) Date of Patent: *Dec. 29, 2020

(54) SURGICAL INSTRUMENT AND DRIVE MECHANISM THEREOF

(71) Applicant: REACH SURGICAL INC., Tianjin (CN)

(72) Inventors: Jean Beaupré, Cincinnati, OH (US); Jiaquan Dong, Tianjin (CN)

(73) Assignee: Reach Surgical Inc., Tianjin (CN)

( * ) Notice: Subject to any disclaimer, the term of this patent is extended or adjusted under 35 U.S.C. 154(b) by 149 days.

This patent is subject to a terminal disclaimer.

(21) Appl. No.: 16/162,479

(22) Filed: Oct. 17, 2018

(65) Prior Publication Data

US 2019/0046194 A1   Feb. 14, 2019

Related U.S. Application Data

(63) Continuation of application No. 14/972,408, filed on Dec. 17, 2015, now Pat. No. 10,130,364, which is a
(Continued)

(30) Foreign Application Priority Data

Jun. 20, 2013   (CN) .......................... 2013 1 0247715

(51) Int. Cl.
*A61B 17/072*   (2006.01)
*F16D 41/16*   (2006.01)
(Continued)

(52) U.S. Cl.
CPC ........ *A61B 17/07207* (2013.01); *F16D 41/16* (2013.01); *F16H 1/28* (2013.01);
(Continued)

(58) Field of Classification Search
CPC ...... A61B 17/07207; A61B 2090/0818; A61B 2017/00407; A61B 2017/2946;
(Continued)

(56) References Cited

U.S. PATENT DOCUMENTS 5,556,009 A   9/1996 Motzko
5,653,374 A   8/1997 Young et al.
(Continued)

FOREIGN PATENT DOCUMENTS

EP   2145588 A1   1/2010
WO   2007015239 A2   2/2007

OTHER PUBLICATIONS

European Search Report for EP 14 81 3414 dated Sep. 30, 2016.

*Primary Examiner* — Robert F Long
(74) *Attorney, Agent, or Firm* — Arent Fox LLP; Michael Fainberg (57) ABSTRACT

A surgical instrument and a drive mechanism, the drive mechanism includes a motor, a planetary gear train, and a bidirectional ratchet mechanism; the input sun gear of the planetary gear train engages the output shaft of the motor; an output carrier of the planetary gear train engages an executing mechanism of the surgical instrument through a transmission mechanism; the bidirectional ratchet mechanism includes a ratchet, a bidirectional pawl assembly, and a selector; the ratchet is in rigid connection with an annular gear of the planetary gear train; the bidirectional pawl assembly includes a bidirectional pawl; the selector selectively drives a first end or a second end of the bidirectional pawl to bias the ratchet, so as to prevent corresponding rotation of the ratchet when the motor drives the planetary gear train, and allow corresponding rotation of the ratchet when the transmission mechanism drives the planetary gear train.

15 Claims, 7 Drawing Sheets

Related U.S. Application Data continuation of application No. PCT/CN2014/080279, filed on Jun. 19, 2014.

(51) Int. Cl.
| | |
|---|---|
| *F16H 3/44* | (2006.01) |
| *F16H 1/28* | (2006.01) |
| *A61B 17/00* | (2006.01) |
| *A61B 17/29* | (2006.01) |
| *A61B 90/00* | (2016.01) |

(52) U.S. Cl.
CPC ...... *F16H 3/44* (2013.01); *A61B 2017/00398* (2013.01); *A61B 2017/00407* (2013.01); *A61B 2017/00734* (2013.01); *A61B 2017/2923* (2013.01); *A61B 2017/2946* (2013.01); *A61B 2090/0818* (2016.02)

(58) Field of Classification Search
CPC .. A61B 2017/2923; A61B 2017/00734; A61B 2017/00398; F16H 3/44; F16H 1/28; F16D 41/16
USPC .............................. 227/175.1–182.1
See application file for complete search history.

(56) References Cited

U.S. PATENT DOCUMENTS

| | | | |
|---|---|---|---|
| 5,667,517 A | 9/1997 | Hooven | |
| 5,779,130 A | 7/1998 | Alesi et al. | |
| 5,954,259 A | 9/1999 | Viola et al. | |
| 6,264,087 B1 | 7/2001 | Whitman | |
| 6,505,768 B2 | 1/2003 | Whitman | |
| 7,114,642 B2 | 10/2006 | Whitman | |
| 7,422,139 B2 | 9/2008 | Shelton, IV et al. | |
| 7,461,767 B2 | 12/2008 | Viola et al. | |
| 7,556,185 B2 | 7/2009 | Viola | |
| 7,648,055 B2 | 1/2010 | Marczyk | |
| 7,690,530 B2 | 4/2010 | Schneider | |
| 7,743,960 B2 | 6/2010 | Whitman et al. | |
| 7,766,210 B2 | 8/2010 | Shelton, IV et al. | |
| 7,832,611 B2 | 11/2010 | Boyden et al. | |
| 7,922,061 B2 | 4/2011 | Shelton, IV et al. | |
| 7,950,560 B2 | 5/2011 | Zemlock et al. | |
| 7,963,431 B2 | 6/2011 | Scirica | |
| 8,020,742 B2 * | 9/2011 | Marczyk .......... A61B 17/07207 227/175.1 |
| 8,074,858 B2 | 12/2011 | Marczyk | |
| 8,118,207 B2 * | 2/2012 | Racenet ................ A61B 34/71 227/180.1 |
| 8,186,555 B2 | 5/2012 | Shelton, IV et al. | |
| 8,210,413 B2 | 7/2012 | Whitman et al. | |
| 8,245,899 B2 | 8/2012 | Swensgard et al. | |
| 8,292,155 B2 | 10/2012 | Shelton, IV et al. | |
| 8,453,907 B2 | 6/2013 | Laurent et al. | |
| 8,453,914 B2 | 6/2013 | Laurent | |
| 8,459,523 B2 | 6/2013 | Whitman | |
| 8,490,852 B2 | 7/2013 | Viola | |
| 8,540,130 B2 | 9/2013 | Moore et al. | |
| 8,632,535 B2 | 1/2014 | Shelton, IV et al. | |
| 8,646,657 B2 | 2/2014 | Hsu | |
| 8,684,247 B2 * | 4/2014 | Scirica .............. A61B 17/0682 227/175.1 |
| 8,695,866 B2 | 4/2014 | Leimbach et al. | |
| 8,708,211 B2 | 4/2014 | Zemlock et al. | |
| 8,708,213 B2 | 4/2014 | Shelton, IV et al. | |
| 8,733,612 B2 | 5/2014 | Ma | |
| 8,746,530 B2 | 6/2014 | Giordano et al. | |
| 8,752,748 B2 | 6/2014 | Whitman et al. | |
| 8,752,749 B2 | 6/2014 | Moore et al. | |
| 8,763,879 B2 | 7/2014 | Shelton, IV et al. | |
| 8,800,837 B2 | 8/2014 | Zemlock | |
| 8,820,603 B2 | 9/2014 | Shelton, IV et al. | |
| 8,820,607 B2 | 9/2014 | Marczyk | |
| 8,827,134 B2 | 9/2014 | Viola et al. | |
| 8,851,354 B2 | 10/2014 | Swensgard et al. | |
| 8,858,571 B2 | 10/2014 | Shelton, IV et al. | |
| 2005/0006432 A1 | 1/2005 | Rancent | |
| 2007/0034670 A1 | 2/2007 | Racenet | |
| 2007/0060952 A1 | 3/2007 | Roby | |
| 2007/0175951 A1 | 8/2007 | Shelton | |
| 2007/0255314 A1 | 11/2007 | Forsberg | |
| 2008/0281336 A1 | 11/2008 | Zergiebel | |
| 2008/0308607 A1 * | 12/2008 | Timm .............. A61B 17/07207 227/176.1 |
| 2009/0194381 A1 | 8/2009 | Samie et al. | |
| 2010/0012702 A1 * | 1/2010 | Marczyk .......... A61B 17/07207 227/175.1 |
| 2010/0089970 A1 * | 4/2010 | Smith ................ A61B 17/068 227/175.1 |
| 2010/0170931 A1 | 7/2010 | Viola | |
| 2011/0068130 A1 * | 3/2011 | Mitrovic ............ B05O 17/0103 222/386 |
| 2011/0240713 A1 | 10/2011 | Scirica | |
| 2011/0272448 A1 | 11/2011 | Scirica | |
| 2012/0165146 A1 | 6/2012 | Samie et al. | |
| 2014/0182420 A1 * | 7/2014 | Chen .................. B25B 13/463 81/57.13 |
| 2016/0074101 A1 * | 3/2016 | Anglese ............ A61B 18/1206 606/47 |

\* cited by examiner

SURGICAL INSTRUMENT AND DRIVE MECHANISM THEREOF

This application is a continuation of U.S. patent application Ser. No. 14/972,408 filed on Dec. 17, 2015, which claims priority to and is a continuation of International Application No. PCT/CN2014/080279, filed on Jun. 19, 2014, designating the United States, and claiming the benefit of Chinese Patent Application No. 201310247715.2, filed with the State Intellectual Property Office of People's Republic of China on Jun. 20, 2013 and entitled "Surgical instrument and drive mechanism thereof". The afore-mentioned patent applications are hereby incorporated by reference in their entireties.

FIELD

The present disclosure relates to medical instruments and particularly to a surgical instrument and a drive mechanism thereof.

BACKGROUND

Figure 1:
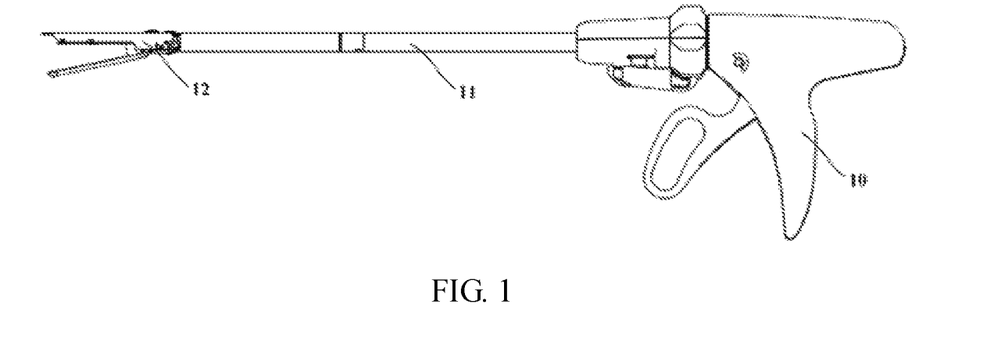
FIG. 1 is a view of a stapling instrument of prior art.

A stapler, which is a surgical instrument widely used in a surgery, has both suturing and cutting functions. As illustrated in FIG. 1, the stapler typically includes a handle 10, a longitudinal portion 11, and an end effector 12, herein the handle 10 provided with a drive mechanism is configured to be held and operated by a surgeon or an operator for controlling and driving, and the distal portion of the handle 10 (a side thereof proximate to the user is the proximate side, and a side thereof away from the user is the distal side) is connected with the end effector 12 through the longitudinal portion 11, and the end effector 12 is configured to be controlled and driven by the handle 10 so as to cut and suture the tissue.

The motor driven stapler is a surgical instrument with which the efficiency and precision of a surgery may be improved, where a motor arranged in the handle is configured as a power source for driving a transmission mechanism so as to further control a pair of jaw members of the end effector to open or close, as well as to control the instrument to advance or retract.

However, if the motor driven stapler fails during operation, for example, a battery is exhausted or the motor fails, then the operations, for example, cutting or suturing, may not be further performed, and it may be difficult to open and retract the instrument manually due to a significant self-resistance of the motor, thus lead to the failure of the procedure; and if the surgical instrument is replaced, then the cost and the risk of the surgery will increase.

SUMMARY

An object of the disclosure is to provide a surgical instrument and a drive mechanism thereof, both of which are power driven and manually driven to thereby reduce the risk and provide a surgeon various operations.

It is provided in the present disclosure a drive mechanism for a surgical instrument, comprising: a motor; a planetary gear train, wherein an input sun gear of the planetary gear train is engaged with an output shaft of the motor, and an output carrier of the planetary gear train is engaged with an executing mechanism of the surgical instrument through a transmission mechanism; and a bidirectional ratchet mechanism comprising a ratchet, a bidirectional pawl assembly, and a stop, wherein the ratchet is in rigid connection with an annular gear of the planetary gear train; the bidirectional pawl assembly comprises a bidirectional pawl; the stop can selectively drive a first end or a second end of the bidirectional pawl to lock the ratchet, so that when the motor drives the planetary gear train, the annular gear of said planetary gear train can be locked from rotating correspondingly, or when the transmission mechanism drives the planetary gear train, the annular gear cannot be locked from rotating correspondingly.

Alternatively, the bidirectional pawl assembly further comprises a pivot and a first torsion spring, wherein the bidirectional pawl is pivotally connected with the pivot, the first torsion spring is sleeved on the pivot with energy stored, and two arms of the first torsion spring are arranged respectively against the bidirectional pawl and a block wall fixed relative to the pivot, so that the second end of the bidirectional pawl is inserted between teeth of the ratchet; and the drive mechanism further comprises a trigger configured to control connection between a power source and the motor, and to control rotation direction of the motor, and the stop is configured as a stop member arranged on the trigger, so that when the trigger is actuated towards the ratchet mechanism, the stop member pushes the first end of the bidirectional pawl to be inserted between teeth of the ratchet.

Alternatively, the stop member is made of elastic material and hinged with the trigger provided with a limiting column that is engaged with a limiting groove of the stop member.

Alternatively, the trigger is provided with a limiting guide groove, and the stop member comprises a pushing element for pushing the first end of the bidirectional pawl, a guiding element that is movable along the limiting guide groove, and a compression spring in connection between the pushing element and the guiding element.

Alternatively, the stop member is made of elastic material and secured to the trigger.

Alternatively, the bidirectional pawl assembly further comprises a pivot, a push button with a protrusion, and a second torsion spring, wherein the bidirectional pawl and the push button are provided with a groove for receiving arms of the second torsion spring; the second torsion spring, the bidirectional pawl and the push button are sleeved on the pivot successively, and two arms of the second torsion spring are arranged against the groove of the bidirectional pawl and the push button; and the drive mechanism further comprises a trigger configured to control the connection between a power source and the motor, and to control the rotation direction of the motor, and the stop is configured as a guide groove arranged on the trigger for cooperating with the protrusion, so that when the trigger is actuated towards the ratchet mechanism, the first end of the bidirectional pawl may be inserted between teeth of the ratchet; when the trigger is actuated away from the ratchet mechanism, the second end of the bidirectional pawl may be inserted between teeth of the ratchet.

Alternatively, the groove of the push button is configured as a C-shaped groove.

Alternatively, the transmission mechanism comprises a rack engaged with the executing mechanism of the surgical instrument, and the drive mechanism further comprises a release member connected with the rack.

Alternatively, a ratch is arranged on a distal portion side of the rack; the drive mechanism further comprises a unidirectional pawl hinged with the trigger, and a third torsion spring sleeved on a pivot of the trigger and the unidirectional pawl, and two arms of the third torsion spring are respectively arranged against the unidirectional pawl and the trigger; and when the trigger is reciprocatively actuated with respect to the ratchet mechanism, the unidirectional pawl pushes the rack distally.

Alternatively, the trigger comprises an advancing trigger portion proximal to the ratchet mechanism, and a retracting trigger portion; and the transmission mechanism further comprises a primary shaft connected with the output carrier of the planetary gear train, a first gear arranged on the primary shaft, and a second gear meshed with the first gear and the rack respectively.

Alternatively, the planetary gear train is a three-stage planetary gear train with three planet gears at each stage.

In another aspect, it is provided in the present disclosure a surgical instrument, comprising the foresaid drive mechanism.

Alternatively, the surgical instrument is an endoscopic stapler.

In the technical solutions according to the disclosure, the stop can be selectively engaged with the first end or the second end of the bidirectional ratchet to lock the ratchet, and when the motor drives the planetary gear train, the stop can lock the ratchet from rotating in corresponding direction, where rotation of the motor can be transferred to the transmission mechanism for electric advancing and retracting; and when the transmission mechanism drives the planetary gear train, the stop can unlock the ratchet from rotating in corresponding direction, where the planetary gear train idles, and no power may be transmitted to the output shaft of the motor, and rotation of the motor will not be transferred to the planetary gear train, thus enabling manual retracting and advancing. Thus, the drive mechanism and the surgical instrument are both power driven and manually driven to thereby reduce the failure risk of surgery and provide the surgeon with various operations.

DETAILED DESCRIPTION

In order to alleviate failure risks of a surgery and to provide various operations, it is provided in one embodiment of the present disclosure a surgical instrument and a drive mechanism thereof. In the present disclosure, the stop can be selectively engaged with the first end or the second end of the bidirectional ratchet to lock the ratchet, and when the motor drives the planetary gear train, the stop can lock the ratchet from rotating in corresponding direction, where the power of the motor can be output to the transmission mechanism for motor advancing and retracting; and when the transmission mechanism drives the planetary gear train into operation, the stop can unlock the ratchet from rotating in corresponding direction, where the planetary gear train idles, and there is no power transmitted to the output shaft of the motor, and rotation of the motor will not be transferred to the planetary gear train, thus enabling manual retracting and advancing. The surgical instrument with the drive mechanism is both power driven and manually driven, which may reduce failure risks of the surgery and provide surgeons with various operations. In order to clearly describe the objectives, technical solutions and advantages of the disclosure, the detailed embodiments of the present disclosure are disclosed herein.

The following reference numerals will be used throughout the present disclosure:

| | | |
|---|---|---|
| 10-handle | 11-longitudinal portion | 12-end effector |
| 13-motor | 14-planetary gear train | 15-sun gear |
| 16-planet gear | 17-annular gear | 18-end cap |
| 19-carrier | 20-ratchet | 21-bidirectional pawl |
| 22-first end | 23-second end | 24-pivot |
| 25a-first torsion spring | 25b-second torsion spring | 25c-third torsion spring |
| 26-trigger | 27-stop member | 28-limiting guide groove |
| 29-pushing element | 30-guiding element | 31-compression spring |
| 32-push button | 33-groove for receiving spring arm | 34-protrusion |
| 35-guide groove | 36-rack | 37-releasing member |
| 38-ratch | 39-unidirectional pawl | 41-advancing trigger portion |
| 42-retracting trigger portion | 43-primary shaft | 44-first gear |
| 45-second gear | 46-limiting column | 47-limiting groove |

Figure 2A:
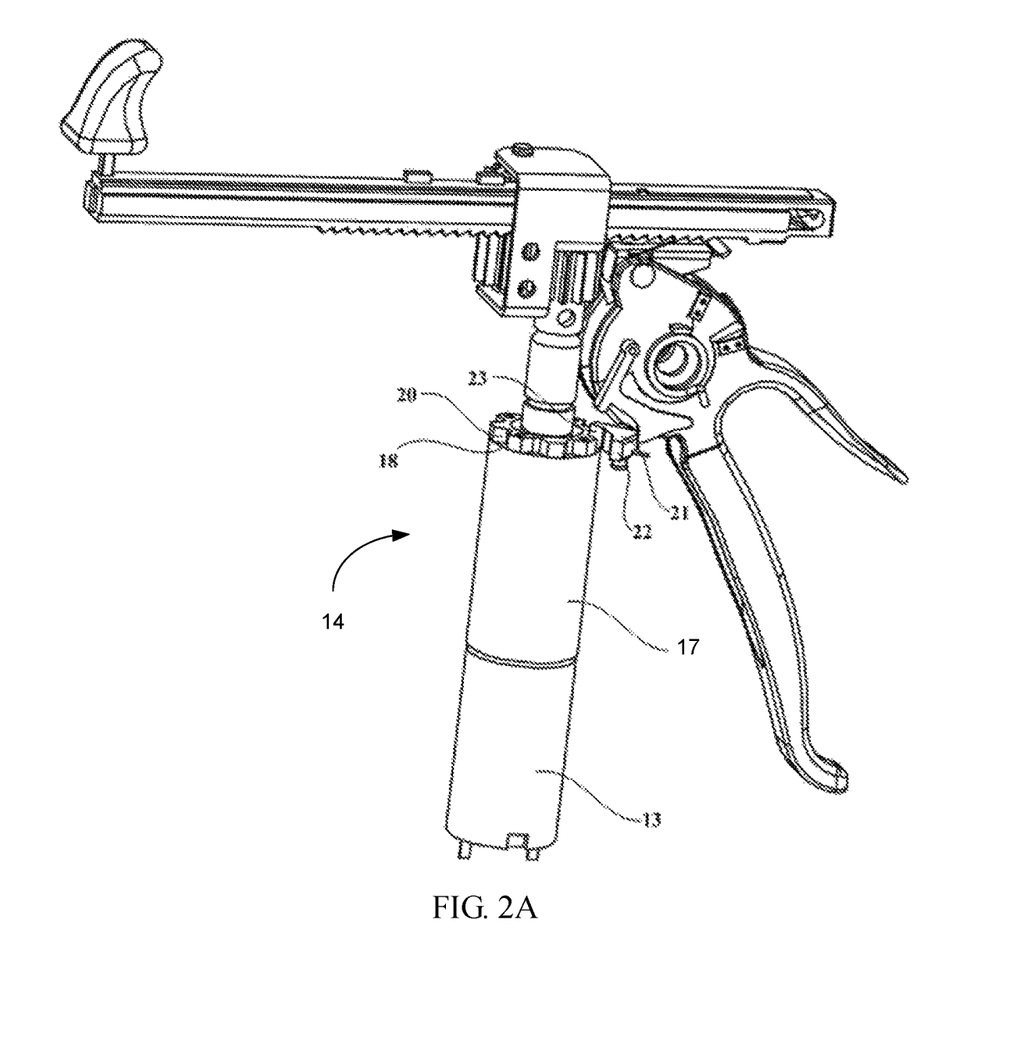
FIG. 2A is a view of a drive mechanism according to an embodiment of the present disclosure.
Figure 2B:
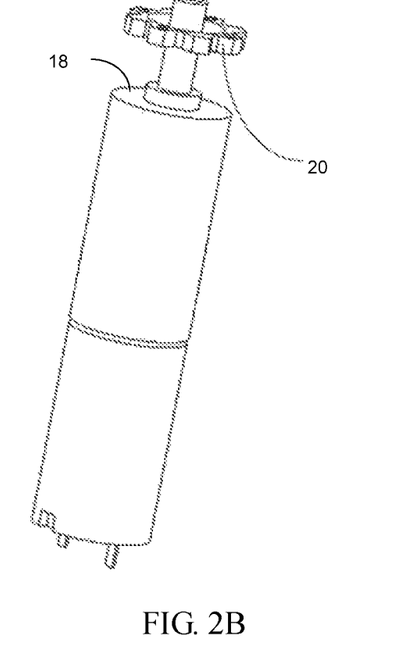
FIG. 2B is another view of a drive mechanism according to an embodiment of the present disclosure.

As illustrated in FIG. 2A and FIG. 2B, a drive mechanism of a surgical instrument according to one embodiment of the disclosure includes following elements.

A motor 13.

A planetary gear train 14, where an input sun gear of the planetary gear train 14 is engaged with an output shaft of the motor 13, and an output carrier of the planetary gear train 14 is engaged with an executing mechanism of the surgical instrument through a transmission mechanism.

A bidirectional ratchet mechanism including a ratchet 20, a bidirectional pawl assembly, and a stop, where the ratchet 20 is in rigid connection with an annular gear 17 of the planetary gear train 14; the bidirectional pawl assembly includes a bidirectional pawl 21, and the stop selectively drives a first end 22 or a second end 23 of the bidirectional pawl 21 to lock the ratchet 20, so that the ratchet 20 will be locked from rotating when the motor 13 drives the planetary gear train 14, and the ratchet 20 will not be locked from rotating when the transmission mechanism drives the planetary gear train 14.

In various embodiments of the disclosure, there is no limitation on types of surgical instruments having the drive mechanism, which could be, for example, a purse-string forceps, a stapler, etc., which may be actuated to open or close, or advance or retract. Throughout this description, the term "distal" refers to the portion of the instrument furthest from the operator, and the term "proximal" refers to the portion of the instrument closest to the operator. The term "advancing" refers to moving distally, and the term "retracting" refers to moving proximately. The term "rotate forward" and "rotate backward" can be defined particularly in different embodiments, for example, in one embodiment, the term "rotate forward" refers to rotate clockwise, and the term "rotate backward" refers to rotate counterclockwise, vice versa.

The planetary gear train has been widely applied in the fields of medical instruments, for example, due to its compact structure, small return stroke gap, large rated output torsion, high precision, and long service lifetime. The planetary gear train can be designed as a multiple-stage gear train based on different gear ratios, for example, 1-stage gear train, 2-stage gear train, 3-stage gear train, etc. In order to match the gear ratio of the planetary gear train with requirements of the surgical instrument for standardized surgeries, the planetary gear train 14 of the drive mechanism according to one embodiment of the disclosure is preferably configured as a three-stage planetary gear train including three planet gears at each stage.

Figure 3:
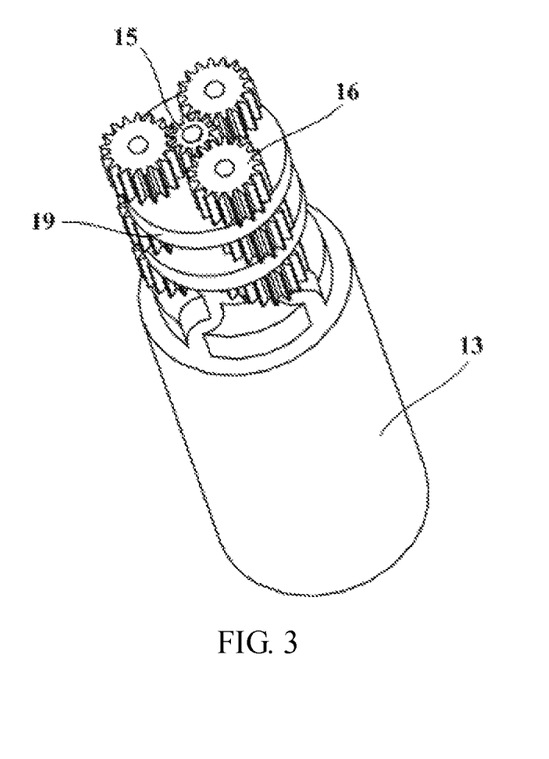
FIG. 3 is a view of transmission connection between a motor and a planetary gear train.

As illustrated in FIG. 3, the three-stage planetary gear train (the annular gear, the end cap, and the third stage carrier, etc., are not shown for better showing internal structure) includes a sun gear 15, a plurality of planet gears 16, and a carrier 19 at each stage, wherein the sun gear of the first stage is engaged with the output shaft of the motor 13; each of the three planet gears of the first stage meshes with the sun gear of the first stage, respectively; the carrier of the first stage is engaged with the sun gear of the second stage; each of the three planet gears of the second stage meshes with the sun gear of the second stage; the carrier of the second stage is engaged with the sun gear of the third stage, and each of the three planet gears of the third stage meshes with the sun gear of the third stage, and the carrier of the third stage (i.e., the output carrier) is engaged with the transmission mechanism, and all of the planet gears mesh with the annular gear, respectively (the annular gear is a gear with inner teeth, and in the planetary gear train 14, the planet gears 16 are arranged inside and mesh with the annular gear 17). In this embodiment, the planetary gear train 14 includes an end cap 18 secured to the annular gear 17, and the ratchet 20 is secured to the end cap 18, so that the ratchet 20 is in rigid connection with the annular gear 17. In one embodiment of the present disclosure, the ratchet 20 can alternatively be secured to the annular gear 17 in different ways; for example, the ratchet can be fixed directly on the surface of the annular gear through soldering, bolting, etc.

The drive mechanism operates as follows.

The bidirectional pawl 21 may swing about a pivot through the bidirectional ratchet mechanism, so that one end thereof may be selectively engaged with the ratchet 20, which is adapted to further lock the ratchet 20 from rotating in a corresponding direction, and allow the ratchet 20 to rotate in the opposite direction, vice versa. Typically the ratchet 20 of the bidirectional ratchet mechanism is provided with symmetrical teeth, e.g., with rectangle teeth, and the pawl 21 is provided with two ends that could be distributed symmetrically or asymmetrically. In the present disclosure, the pawl 21 is symmetry.

In one of the embodiments of the present disclosure, more specifically, "rotate/rotating in corresponding direction" refers to: when the motor 13 rotates forward, the ratchet 20 tends to rotate backward (if the ratchet is not locked at this time, then the ratchet will be driven by the motor 13 to rotate backward, so that the planetary gear train 14 will idle, and rotation of the motor 13 will not be transferred to the transmission mechanism); and alike, when the motor 13 rotates backward, the ratchet 20 tends to rotate forward (if the ratchet is not locked at this time, then the ratchet will be driven to rotate forward by the motor 13, so that the planetary gear train 14 will idle, and rotation of the motor 13 will not be transferred to the transmission mechanism); and when the transmission mechanism drives the output carrier of the planetary gear train 14 to rotate forward, the ratchet 20 tends to rotate forward (if the ratchet is not locked at this time, then it will be driven by the transmission mechanism to rotate forward, so that the planetary gear train 14 will idle, and rotation of the motor 13 will not be transferred to the transmission mechanism); and alike, when the transmission mechanism drives the output carrier of the planetary gear train 14 to rotate backward, the ratchet tends to rotate backward (if the ratchet is not locked at this time, then it will be driven by the transmission mechanism to rotate backward, so that the planetary gear train 14 will idle, and rotation of the motor 13 will not be transferred to the transmission mechanism).

When the motor 13 rotates, the ratchet 20 is locked from rotating in corresponding direction by the pawl 21, and since the ratchet 20 in rigid connection with the annular gear 17, the annular gear 17 will not rotate neither (in the circumstance that when the motor 13 drives the planetary gear train 14, the annular gear 17 tends to rotate in an opposite direction with respect to the motor 13). Therefore, the motor 13 drives the sun gear 15, the planet gears 16, and the carrier 19 at each stage to rotate, so as to further drive the transmission mechanism through the third stage carrier.

If the motor 13 fails or is overloaded or otherwise needs to be operated manually, then the transmission mechanism will be driven manually, where the third stage carrier of the planetary gear train 14 will be rotated by the transmission mechanism (i.e. the transmission mechanism drives the planetary gear train 14), and since the rotation tendency of the annular gear 17 and the ratchet 20 when the transmission mechanism drives the planetary gear train 14 is opposite to the rotation tendency thereof when the motor 13 drives the planetary gear train 14, so even if the ratchet 20 is locked before disengaging from the bidirectional pawl 21, the ratchet 20 and the annular gear 17 will not be locked by the bidirectional pawl 21 from rotating in the opposite direction, so that the previous operation (advancing or retracting) can be continued manually, and if the bidirectional pawl 21 is disengaged from the ratchet 20 or locks the ratchet 20 from rotating in the opposite direction, then an operation opposite to the previous operation can be driven manually. Particularly the transmission mechanism will actuate the annular gear 17 (the annular gear 17 rotates in the same direction as the third stage carrier), the planet gears 16 and carrier 19 at each stage, and the second stage and the third stage sun gears to rotate, where the first stage sun gear will not rotate due to rigid connection with the output shaft of the motor 13, the entire planetary gear train 14 will idle, and rotation of the motor 13 will not be transferred to the planetary gear train 14, thus enabling manual advancing or retracting.

Figure 4:
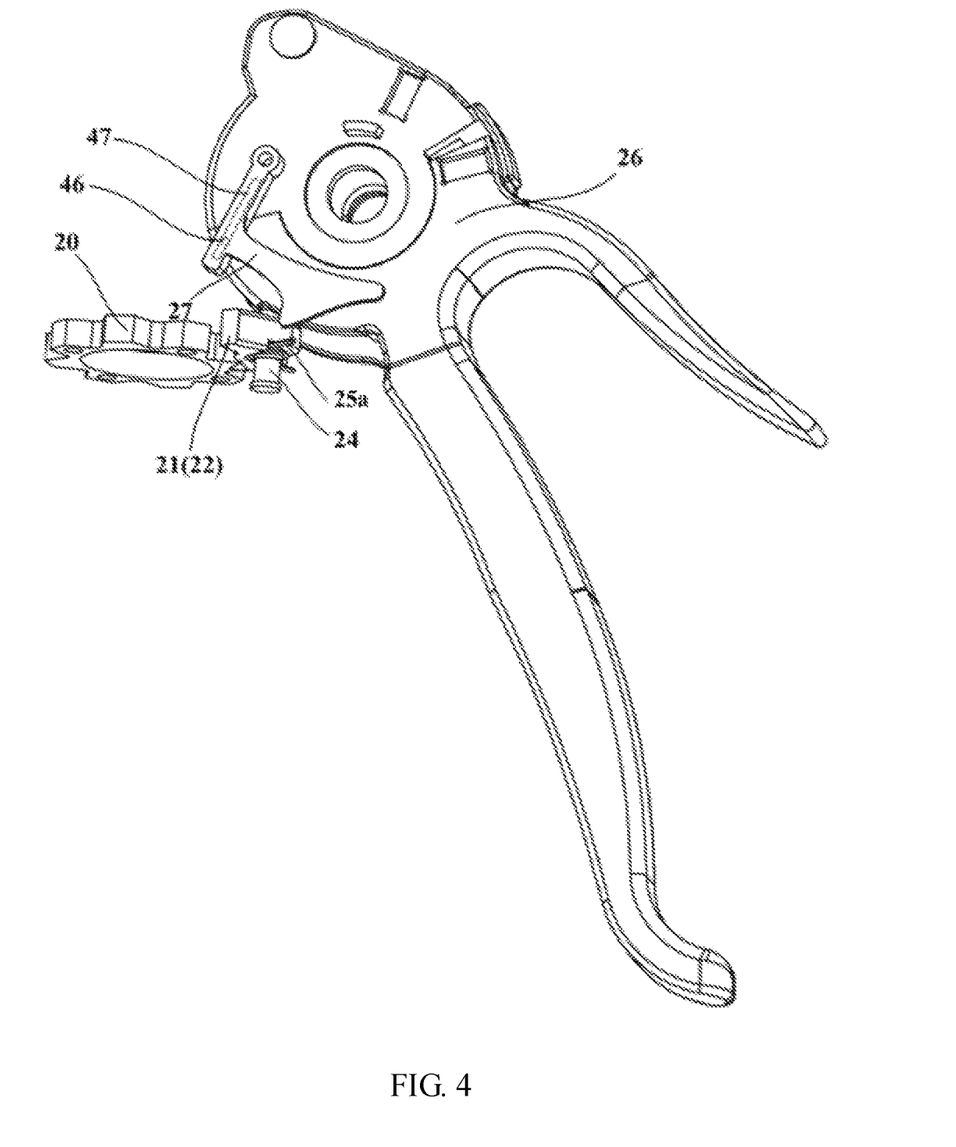
FIG. 4 is a view of a bidirectional ratchet mechanism and a stop member according to a first embodiment of the present disclosure.

As illustrated in FIG. 4, in the preferred embodiment, the bidirectional pawl assembly further includes a pivot 24 and a first torsion spring 25a, wherein the bidirectional pawl 21 is pivotally connected with the pivot 24, the first torsion spring 25a is sleeved on the pivot 24 with energy stored, and two arms of the first torsion spring 25a are respectively arranged against the bidirectional pawl 21 and a block wall fixed relative to the pivot 24, so that the second end 23 of the bidirectional pawl 21 is inserted between teeth of the ratchet 20 to lock the ratchet 20 from rotating in one direction.

The driving mechanism further includes a trigger 26 configured to control connection between a power source and the motor 13, and to control the rotation direction of the motor 13, and the stop is a stop member 27 arranged on the trigger 26, so that when the trigger 26 is moved toward the ratchet mechanism, the stop member 27 pushes the first end 22 of the bidirectional pawl 21 to be inserted into teeth of the ratchet 20 to lock the ratchet 20 from rotating in the other direction.

The trigger 26 can be configured to control the connection between the power source and the motor 13, and to control the rotation direction of the motor 13 particularly in any applicable manner without being limited thereto, for example, an elastic thimble can be arranged inside the trigger 26, and when the trigger 26 is operated to rotate toward the ratchet mechanism till some angle, the elastic thimble rotates therewith and switches on the advance circuit of the drive mechanism; when the trigger 26 rotates away from the ratchet mechanism till some angle, the elastic thimble rotates therewith and switches on the retract circuit of the drive mechanism; and when the trigger 26 is not operated, the motor 13 will not be connected with the power source.

In this embodiment, the pivot 24 is in fixed connection with a housing of the surgical instrument (the drive mechanism is arranged inside the housing which will not be illustrated for the purpose of showing the structure of the drive mechanism), and the block wall is an inner wall of the housing. It shall be noted that the pivot 24 can alternatively be in fixed connection with a structural component arranged inside the housing, and the block wall can alternatively be a side wall of the structural component inside the handle housing. As illustrated in FIG. 4, at least one portion of the surface of the bidirectional pawl 21 can be designed as a stepped surface, and the first torsion spring 25a can be arranged inside the stepped surface, where the two arms of the first torsion spring 25a are pushed against the stepped surface and the inner wall of the housing, respectively. When the trigger 26 is not actuated, or actuated to rotate away from the ratchet mechanism, the second end 23 of the bidirectional pawl 21 will be inserted between teeth of the ratchet 20 due to the torsion of the first torsion spring 25a. When the trigger 26 is actuated to rotate toward the ratchet mechanism, the stop member 27 pushes the first end 22 of the bidirectional pawl 21 to be inserted between teeth of the ratchet 20. Thus in this embodiment, the bidirectional pawl 21 can be positioned respectively in two states.

Figure 5:
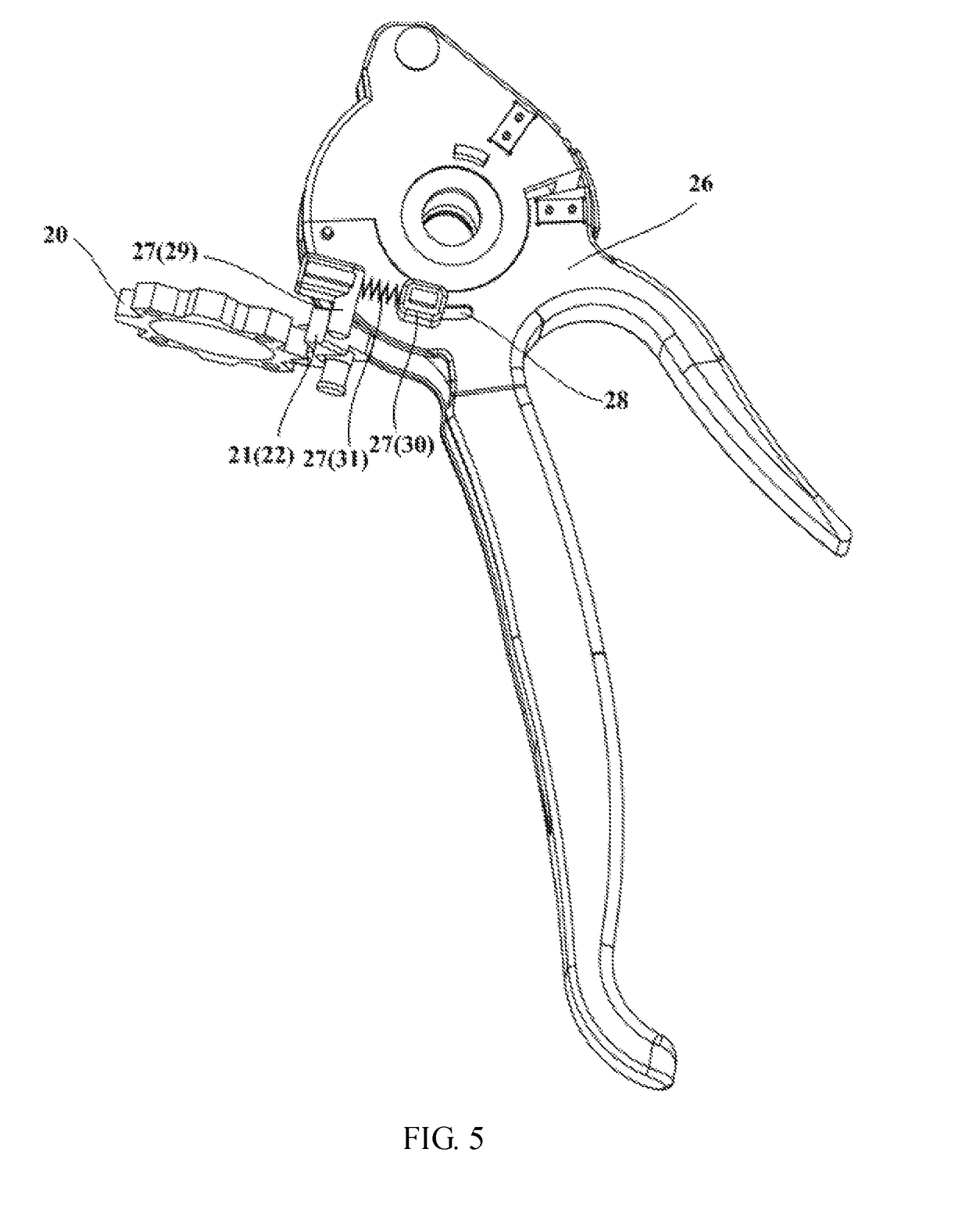
FIG. 5 is a view of a bidirectional ratchet mechanism and a stop member according to a second embodiment of the present disclosure.
Figure 6:
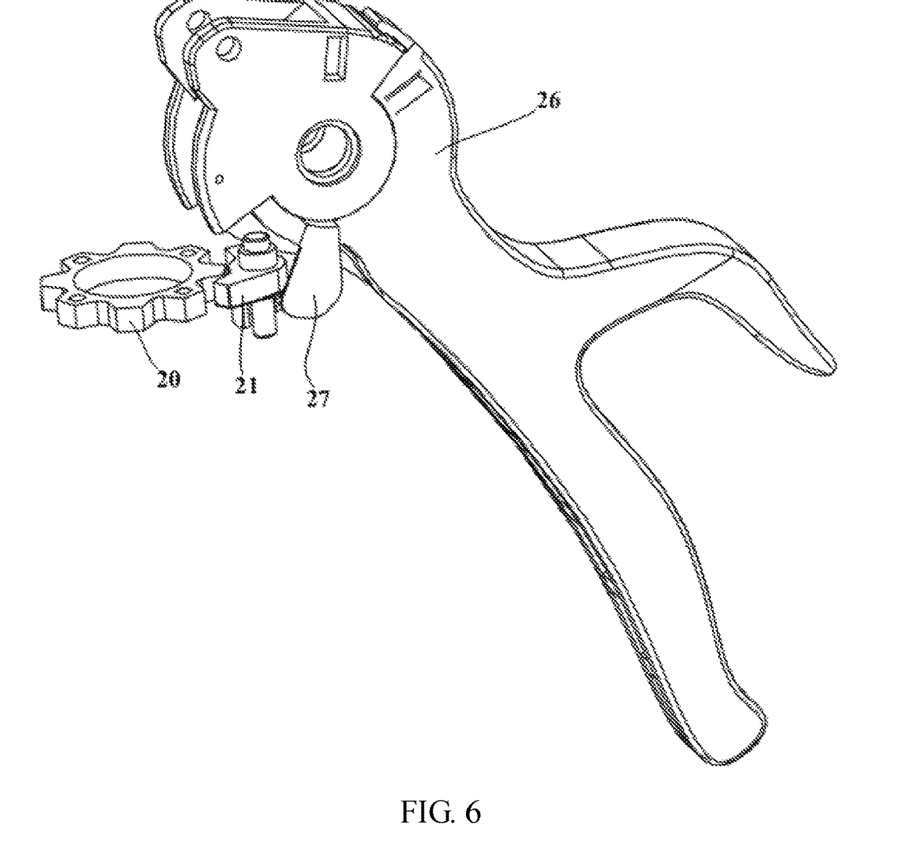
FIG. 6 is a view of a bidirectional ratchet mechanism and a stop member according to a third embodiment of the present disclosure.

The stop member 27 can selectively drive either end of the bidirectional pawl 21 so as to lock the ratchet 20 from rotating accordingly, and when the trigger 26 is reset, the stop member 27 arranged on the trigger 26 will be reset together with the trigger 26, where the stop member 27 no longer pushes the first end 22 of the bidirectional pawl 21, and the bidirectional pawl 21 may be reset to initial position by the first torsion spring 25a (where the second end 23 of the bidirectional pawl 21 is inserted between teeth of the ratchet 20). There is no limitation on structure of the stop member 27, for example, in the embodiment illustrated in FIG. 4, the stop member 27 is configured as a stop member made of elastic material and hinged jointed with the trigger 26 provided with a limiting column 46, and the stop member 27 is provided with a limiting groove 47 engaging with the limiting column 46 (the limiting column 46 and the limiting groove 47 hidden inside the stop member 27 are represented in dotted lines as illustrated). In another example, in the embodiment illustrated in FIG. 5, the trigger 26 is provided with a limiting guide groove 28, and the stop member 27 includes a pushing element 29 adapted for pushing the first end 22 of the bidirectional pawl 21, a guiding element 30 movable along the limiting guide groove 28, and a compression spring 31 in connection with the pushing element 29 and the guiding element 30. In still another embodiment illustrated in FIG. 6, the stop member 27 is configured as a stop member made of elastic material and in fixed connection with the trigger 26. In any of the embodiments, the stop member 27 can selectively drive either end of the bidirectional pawl 21 so as to lock the ratchet 20 from rotating accordingly, as well as being reset together with the trigger 26; in addition, when the stop member 27 is pushed toward the first end 22 of the bidirectional pawl 21, the first end 22 can lock the ratchet 20 from rotating in one direction; while the ratchet 20 will not be locked from rotating in the other direction, that is, the ratchet 20 can rotate in the other direction to thereby push the first end 22 away, where the first end 22 applies a counter-acting force to the stop member 27 that causes elastic deformation of the stop member 27 to thereby facilitate the ratchet 20 rotating in unrestricted direction via reducing resistance against rotation.

Figure 7:
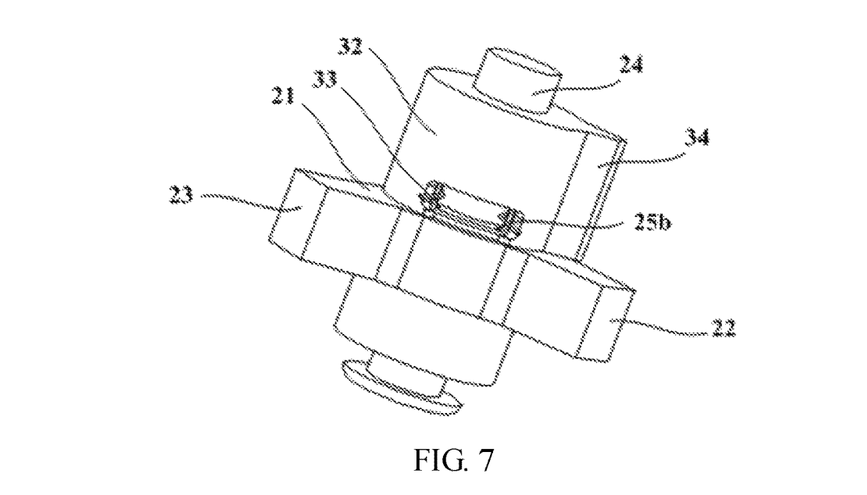
FIG. 7 is a view of a ratchet mechanism according to a fourth embodiment of the present disclosure.
Figure 8:
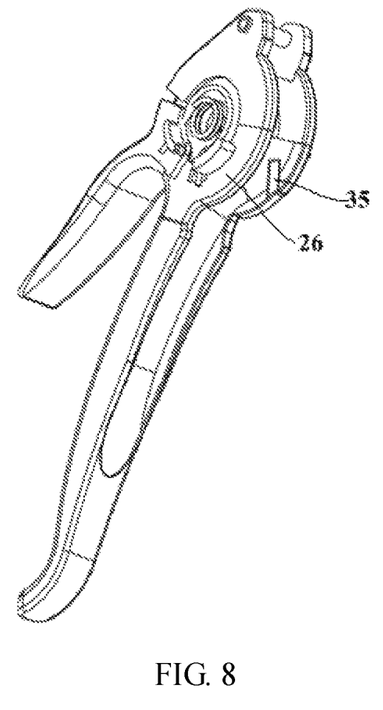
FIG. 8 is a view of a trigger according to the fourth embodiment of the present disclosure.

Referring to FIG. 7 and FIG. 8, FIG. 7 illustrates another embodiment of the ratchet assembly. The bidirectional pawl assembly further includes a pivot 24, a push button 32 with a protrusion 34, and a second torsion spring 25b, where the bidirectional pawl 21 and the push button 32 are provided with a groove 33 for receiving arms of the second torsion spring 25b; the second torsion spring 25b, the bidirectional pawl 21 and the push button 32 are sleeved on the pivot 24 successively, and two arms of the second torsion spring 25b are arranged against the groove 33 of the bidirectional pawl 21 and the push button 32.

The drive mechanism further includes a trigger 26 configured to control the connection between the power source and the motor 13, and to control the rotation direction of the motor 13, and the stop is configured as a guide groove 35 arranged on the trigger 26 to cooperate with the protrusion 34, so that when the trigger 26 is moved toward the ratchet mechanism, the first end 22 of the bidirectional pawl 21 is inserted between teeth of the ratchet 20 to lock the ratchet 20 from rotating in one direction, and when the trigger 26 is moved away from the ratchet mechanism, the second end 23 of the bidirectional pawl 21 is inserted between teeth of the ratchet 20 to lock the ratchet 20 from rotating in the other direction.

In this embodiment, the pivot 24 can be fixed in any applicable manner, for example, the pivot 24 can be fixed to the housing of the surgical instrument, and the second torsion spring 25b can be configured as a C-shaped spring. When the trigger 26 is not actuated, neither the first end 22 nor the second end 23 of the bidirectional pawl 21 contacts with the ratchet 20, so that the ratchet 20 will not be locked from rotating in either direction. When the trigger 26 is actuated toward the ratchet mechanism, the trigger 26 pushes the push button 32 to rotate, so that the groove 33 of the push button 32 compresses one arm of the second torsion spring 25b, and the other arm of the second torsion spring 25b will push the groove 33 of the bidirectional pawl 21 to thereby push the first end 22 of the bidirectional pawl 21 to be inserted between teeth of the ratchet 20. Alike when the trigger 26 is actuated away from the ratchet mechanism, the second end 23 of the bidirectional pawl 21 is inserted between teeth of the ratchet 20. Thus in this embodiment, the bidirectional pawl 21 can be positioned in the three states, respectively.

Further referring to FIG. 7, the groove 33 of the push button 32 is C-shaped. When there is a significant assembly gap between the bidirectional pawl 21 and the push button 32, the second torsion spring 25b can be prevented from falling down to thereby make the surgical procedure instrument more reliable in structure.

Figure 9:
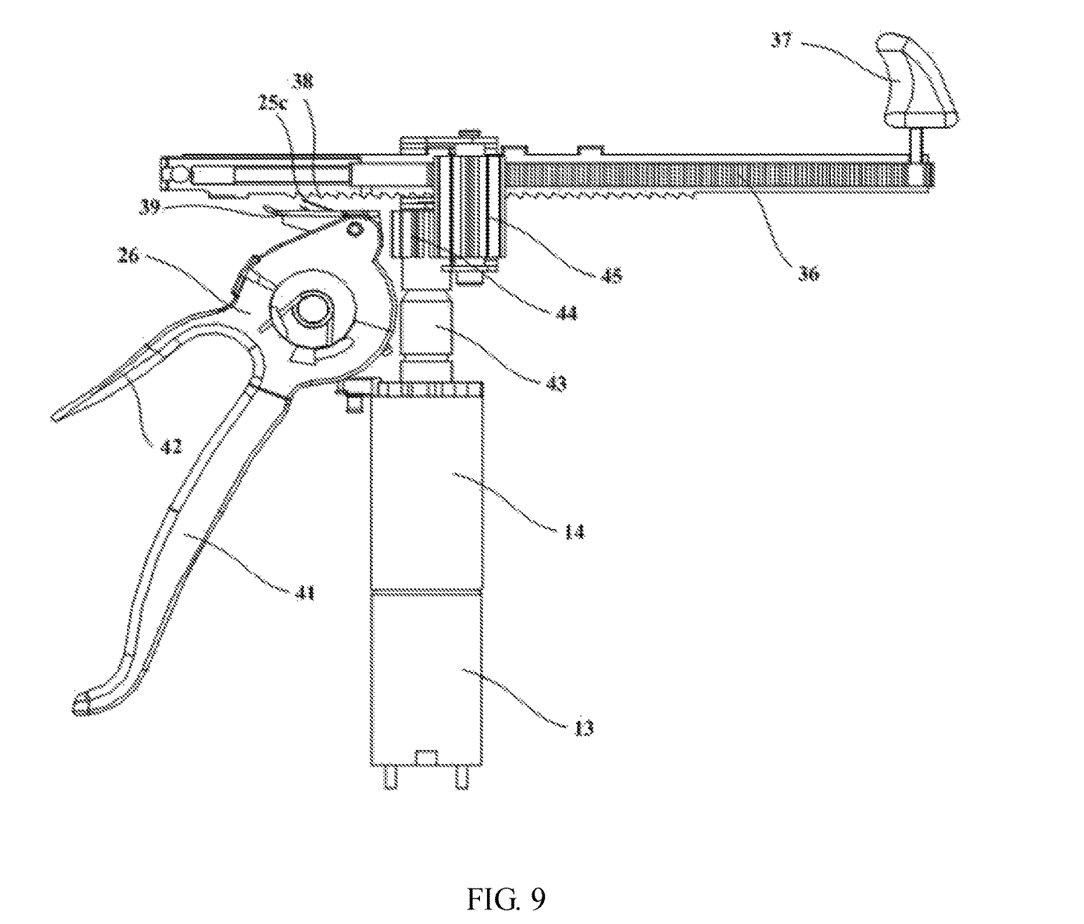
FIG. 9 is a view of a transmission mechanism according to an embodiment of the present disclosure.

As illustrated in FIG. 9, the transmission mechanism includes a transmission assembly engaged with the executing mechanism of the surgical instrument, and in this embodiment, the transmission assembly is a rack 36 provided with teeth, and the drive mechanism further comprises a release member 37 engaged with the rack 36.

Particularly, the release member 37 can be connected with the rack 36 by a metal pin. For manually retracting the instrument, if the ratchet 20 is not locked from rotating in corresponding direction, then the release member 37 can be pulled proximately to thereby retract the rack 36, so that the executing mechanism engaged with the rack 36 is retracted (for example, a cutting knife or a closed assembly of an end effector in a stapler is retracted) to thereby retract the instrument manually. If the trigger 26 is not actuated, in any embodiment illustrated in FIG. 4, FIG. 5, FIG. 6 or FIG. 7, the bidirectional pawl 21 will not lock the ratchet 20 from rotating in direction for manually retraction of the instrument, and the planetary gear train 14 will idle, thus rotation of the motor 13 will not be transferred to the planetary gear train 14.

Further referring to FIG. 9, a ratch 38 is arranged on a distal portion of the rack 36; the drive mechanism further includes a unidirectional pawl 39 hinged with the trigger 26, and a third torsion spring 25c sleeved on the pivot of the trigger 26 and the unidirectional pawl 39, and two arms of the third torsion spring 25c are respectively arranged against the unidirectional pawl 39 and the trigger 26, so that the unidirectional pawl 39 is inserted between teeth of the ratch 38 (FIG. 9 is an assembly drawing in which the third torsion spring 25c is positioned in a natural state; however the third torsion spring 25c is compressed during assembling, so that the unidirectional pawl 39 is inserted between teeth of the ratch 38, and the third torsion spring 25c is invisible in the side view); and when the trigger 26 is actuated reciprocatively with respect to the ratchet mechanism, the unidirectional pawl 39 pushes the rack 36 to move distally.

For manually advancing the instrument, actuating the trigger 26 reciprocatively with respect to the ratchet mechanism, so that the unidirectional pawl 39 pushes the rack 36 to move distally. In any embodiment illustrated in FIG. 4, FIG. 5, FIG. 6 or FIG. 7, the bidirectional pawl 21 will not lock the ratchet 20 from rotating in direction for manually advancing the instrument, the planetary gear train 14 will idle, and rotation of the motor 13 will not be transferred to the planetary gear train 14.

As illustrated in FIG. 9, the trigger 26 includes an advancing trigger portion 41 proximate to the ratchet mechanism, and a retracting trigger portion 42; and the transmission mechanism further includes a primary shaft 43 connected with the output carrier of the planetary gear train 14, a first gear 44 arranged on the primary shaft 43, and a second gear 45 meshed with the first gear 44 and the rack 36, respectively.

It should be noted that there is no limitation on structures of the transmission mechanism, and also there is no limitation on types or quantity of the gears. For advancing the instrument, actuating the advancing trigger portion 41 proximally; for retracting the instrument, actuating the retracting trigger portion 42 distally, which therefore further facilitate accurate operation for the operator. It shall be noted that structure of the trigger 26 will not be limited thereto, for example, the trigger 26 can alternatively include only one trigger portion, or a ring can be arrange within the trigger 26 for the operator's hand to grasp so as to advance or retract the instrument via actuating the trigger 26 back and forth. Taking the embodiment illustrated in FIG. 4 as an example, assuming the motor 13 rotating forward and backward refers to rotating clockwise and counterclockwise respectively, then there are four operating modes of the drive mechanism.

The first operating mode relates to electric advancement. Grasping the advancing trigger portion 41 towards the ratchet mechanism, where the motor 13 rotates forward. The first end 22 of the bidirectional pawl 21 locks the ratchet 20 from rotating backward but does not lock the ratchet 20 from rotating forward (that is, rotation for electric advancing is locked, and manual rotation for advancing is not locked). The rotation of the motor 13 is transferred by the planetary gear train 14 to the transmission mechanism, and the output carrier of the planetary gear train 14, the primary shaft 43, and the first gear 44 rotate forward, while the second gear 45 rotates backward, so as to drive the rack 36 moving distally, thus accomplish electric advancement.

The second operating mode relates to electric retraction. Pushing the retracting trigger portion 42 away from the ratchet mechanism, where the motor 13 rotates backward. The second end 23 of the bidirectional pawl 21 locks the ratchet 20 from rotating forward but does not lock the ratchet 20 from rotating backward (that is, rotation for electric retracting is locked, and rotation for manual retracting is not locked). The rotation of the motor 13 is transferred by the planetary gear train 14 to the transmission mechanism, and the output carrier of the planetary gear train 14, the primary shaft 43, and the first gear 44 rotate backward, while the second gear 45 rotates forward, so as to drive the rack 36 moving proximally, thus enabling electric retraction.

The third operating mode relates to manual advancement. If the motor 13 fails or is such overloaded as to need manual assistance or otherwise needs to be advanced manually, the advancing trigger portion 41 may be grasped reciprocatively with respect to the ratchet mechanism, more specifically, when pressing the advancing trigger portion 41 proximally, the unidirectional pawl 39 pushes the rack 36 moving distally, the second gear 45 rotates backward, and the output carrier of the planetary gear train 14, the primary shaft 43, and the first gear 44 rotate forward, as well as the first end 22 of the bidirectional pawl 21 locks the ratchet 20 from rotating backward as well as allowing the ratchet 20 rotating forward (that is, rotation for manual advancing is not locked). In addition, the first end 22 of the bidirectional pawl 21 will be bounced off by the ratchet (where the elastic stop member 27 will also be deformed elastically accordingly). The planetary gear train 14 idles, and rotation of the motor 13 will not be transferred to the planetary gear train 14, thus enabling manual advancing of the instrument. When releasing the advancing trigger portion 41, in the embodiments illustrated in FIG. 4, FIG. 5 and FIG. 6, the second end 23 of the bidirectional pawl 21 is inserted between teeth of the ratchet 20, and the ratchet 20 is locked from rotating forward due to the inertia and not locked from rotating backward (that is, rotation for manual retracting is not locked, where the elastic deformation of the stop member 27 will eliminate). In the embodiment illustrated in FIG. 7, when the advancing trigger portion 41 is released, the bidirectional pawl 21 has no contact with the ratchet 20, and the ratchet 20 will not be locked in either direction but can still rotate forward due to the inertia.

If manual advancing needs to be driven through the release member 37, it can be achieved through pushing the release member 37 distally as well as pressing the trigger 26 toward the ratchet mechanism (that is, rotation of the ratchet 20 for manual advancing is not locked).

The fourth operating mode relates to manual retraction. On the occasion of the motor 13 fails or otherwise needs to be retracted manually, actuating the release member 37 proximately, where the rack 36 is retracted, the second gear 45 rotates forward, and the output carrier of the planetary gear train 14, the primary shaft 43, and the first gear 44 rotate backward, and at this time if the trigger 26 is not actuated, in the embodiments illustrated in FIG. 4, FIG. 5 and FIG. 6, the second end 23 of the bidirectional pawl 21 will not lock the ratchet 20 from rotating backward (that is, rotation for manual retracting is not locked). In addition, the second end 23 of the bidirectional pawl 21 will be bounced off by the ratchet 20; and in the embodiment illustrated in FIG. 7, the bidirectional pawl 21 has no contact with the ratchet 20, and the ratchet 20 will not be locked in either direction, so the planetary gear train 14 idles, and no resistance of the motor 13 will be transferred to the planetary gear train 14, thus enabling manual retraction of the instrument.

As described above, the stop can selectively drive the first end 22 or the second end 23 of the bidirectional ratchet 21 to lock the ratchet 20, and when the motor 13 drives the planetary gear train 14, the stop can lock the ratchet 20 from rotating in corresponding direction, where rotation of the motor 13 can be transferred to the transmission mechanism for electric advancing and retracting; when the transmission mechanism drives the planetary gear train 14, the stop can unlock the ratchet 20 from rotating in corresponding direction, where the planetary gear train 14 idles, thus rotation will not be transferred to the output shaft of the motor 13, and rotation of the motor will not be transferred to the planetary gear train 14 neither, which enabling manual retracting and advancing. In one of the embodiments of the present disclosure, the drive mechanism and the surgical instrument are selectively power driven and manually driven, which may reduce the risk of the surgery and provide surgeons with various operations.

It is further provided in the present disclosure a surgical instrument including the drive mechanism according to any one of the embodiments above. It should be noted that there is no limitation on types of the surgical instrument. For example, in one embodiment, the surgical instrument is an endoscopic stapler. The surgical instrument according to the embodiment of the disclosure is selectively power driven and manually driven, which may reduce risk of surgery and provide surgeons with various operations.

Evidently those skilled in the art can make various modifications and variations to the disclosure without departing from the spirit and scope of the disclosure. Thus the disclosure is also intended to encompass these modifications and variations thereto so long as the modifications and variations come into the scope of the claims appended to the disclosure and their equivalents.

What is claimed is:

1. A drive mechanism for a surgical instrument, comprising:
a motor;
a planetary gear train, wherein an input sun gear of said planetary gear train is engaged with an output shaft of said motor, and an output carrier of said planetary gear train is engaged with an executing mechanism of said surgical instrument through a transmission mechanism; and
a bidirectional ratchet mechanism comprising a ratchet, a bidirectional pawl assembly, and a selector, wherein said ratchet is in rigid connection with an annular gear of said planetary gear train; said bidirectional pawl assembly comprises a bidirectional pawl; said selector can selectively drive a first end or a second end of said bidirectional pawl to lock either of two opposite directions of rotation of said ratchet, and when said planetary gear train is driven by said motor, said annular gear of said planetary gear train can be prevented from rotating in a corresponding direction, or when said planetary gear train is driven manually through said transmission mechanism, said annular gear is allowed to rotate in a corresponding direction;
wherein:
said bidirectional pawl assembly further comprises a pivot, a push button with a protrusion, and a second torsion spring, wherein said bidirectional pawl and said push button are provided with a groove for receiving arms of said second torsion spring (25b); said second torsion spring, said bidirectional pawl and said push button are sleeved on said pivot successively, and two arms of said second torsion spring are arranged against said groove of said bidirectional pawl and said push button; and
said drive mechanism further comprises a trigger configured to control said connection between a power source and said motor, and to control the rotation direction of said motor, and said selector is configured as a guide groove arranged on said trigger for cooperating with said protrusion, so that when said trigger is actuated towards said ratchet mechanism, said first end of said bidirectional pawl may be inserted between teeth of said ratchet; when said trigger is actuated away from said ratchet mechanism, said second end of said bidirectional pawl may be inserted between teeth of said ratchet.

2. The drive mechanism according to claim 1, wherein said groove of said push button is configured as a C-shaped groove.

3. The drive mechanism according to claim 1, wherein said transmission mechanism comprises a rack engaged with said executing mechanism of said surgical instrument, and said drive mechanism further comprises a release member connected with said rack.

4. The drive mechanism according to claim 3, wherein:
a ratch is arranged on a distal portion of said rack;
said drive mechanism further comprises a unidirectional pawl hinged with said trigger, and a third torsion spring sleeved on a pivot of said trigger and said unidirectional pawl, and two arms of said third torsion spring are respectively arranged against said unidirectional pawl and said trigger; and
when said trigger is reciprocately actuated with respect to said ratchet mechanism, said unidirectional pawl pushes said rack distally.

5. The drive mechanism according to claim 4, wherein:
said trigger comprises an advancing trigger portion proximal to said ratchet mechanism, and a retracting trigger portion; and
said transmission mechanism further comprises a primary shaft connected with said output carrier of said planetary gear train, a first gear arranged on said primary shaft, and a second gear meshed with said first gear and said rack respectively.

6. The drive mechanism according to claim 1, wherein said planetary gear train is a three-stage planetary gear train with three planet gears at each stage.

7. A surgical instrument, comprising a drive mechanism, wherein, said driving mechanism comprising:
a motor;
a planetary gear train, wherein an input sun gear of said planetary gear train is engaged with an output shaft of said motor, and an output carrier of said planetary gear train is engaged with an executing mechanism of said surgical instrument through a transmission mechanism; and
a bidirectional ratchet mechanism comprising a ratchet, a bidirectional pawl assembly, and a selector, wherein said ratchet is in rigid connection with an annular gear of said planetary gear train; said bidirectional pawl assembly comprises a bidirectional pawl; said selector can selectively drive a first end or a second end of said bidirectional pawl to lock either of two opposite directions of rotation of said ratchet, and when said planetary gear train is driven by said motor, said annular gear of said planetary gear train can be prevented from rotating in a corresponding direction, or when said planetary gear train is driven manually through said transmission mechanism, said annular gear is allowed to rotate in a corresponding direction.

8. The surgical instrument according to claim 7, wherein, said bidirectional pawl assembly further comprises a pivot and a first torsion spring, wherein said bidirectional pawl is pivotally connected with said pivot, said first torsion spring is sleeved on said pivot with energy stored, and two arms of said first torsion spring are arranged respectively against said bidirectional pawl and a block wall fixed relative to said pivot, so that said second end of said bidirectional pawl is inserted between teeth of said ratchet; and
said drive mechanism further comprises a trigger configured to control connection between a power source and said motor, and to control rotation direction of said motor, and said selector is configured as a selector member arranged on said trigger, so that when said trigger is actuated towards said ratchet mechanism, said selector member pushes said first end of said bidirectional pawl to be inserted between teeth of said ratchet.

9. The surgical instrument according to claim 8, wherein said selector member is made of elastic material and hinged with said trigger provided with a limiting column that is engaged with a limiting groove of said selector member.

10. The surgical instrument according to claim 8, wherein said trigger is provided with a limiting guide groove, and said selector member comprises a pushing element for pushing said first end of said bidirectional pawl, a guiding element that is movable along said limiting guide groove, and a compression spring in connection between said pushing element and said guiding element.

11. The surgical instrument according to claim 7, wherein, said bidirectional pawl assembly further comprises a pivot, a push button with a protrusion, and a second torsion spring, wherein said bidirectional pawl and said push button are provided with a groove for receiving arms of said second torsion spring; said second torsion spring, said bidirectional pawl and said push button are sleeved on said pivot successively, and two arms of said second torsion spring are arranged against said groove of said bidirectional pawl and said push button; and
said drive mechanism further comprises a trigger configured to control said connection between a power source and said motor, and to control the rotation direction of said motor, and said selector is configured as a guide groove arranged on said trigger for cooperating with said protrusion, so that when said trigger is actuated towards said ratchet mechanism, said first end of said bidirectional pawl may be inserted between teeth of said ratchet; when said trigger is actuated away from said ratchet mechanism, said second end of said bidirectional pawl may be inserted between teeth of said ratchet.

12. The surgical instrument according to claim 8, wherein said transmission mechanism comprises a rack engaged with said executing mechanism of said surgical instrument, and said drive mechanism further comprises a release member connected with said rack.

13. The surgical instrument according to claim 12, wherein:
a ratch is arranged on a distal portion of said rack;
said drive mechanism further comprises a unidirectional pawl hinged with said trigger, and a third torsion spring sleeved on a pivot of said trigger and said unidirectional pawl, and two arms of said third torsion spring are respectively arranged against said unidirectional pawl and said trigger; and
when said trigger is reciprocately actuated with respect to said ratchet mechanism, said unidirectional pawl pushes said rack distally.

14. The surgical instrument according to claim 13, wherein:
said trigger comprises an advancing trigger portion proximal to said ratchet mechanism, and a retracting trigger portion; and
said transmission mechanism further comprises a primary shaft connected with said output carrier of said planetary gear train, a first gear arranged on said primary shaft, and a second gear meshed with said first gear and said rack respectively.

15. The surgical instrument according to claim 7, wherein said surgical instrument is an endoscopic stapler.

* * * * *